US008927262B2

(12) United States Patent
Nazareth et al.

(10) Patent No.: US 8,927,262 B2
(45) Date of Patent: *Jan. 6, 2015

(54) OVULATION PREDICTOR TEST

(75) Inventors: Albert R. Nazareth, Mercerville, NJ (US); Timothy Snowden, Howell, NJ (US); Mary Beth Boyle, Pennington, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 736 days.

This patent is subject to a terminal disclaimer.

(21) Appl. No.: 12/897,216

(22) Filed: Oct. 4, 2010

(65) Prior Publication Data

US 2012/0083047 A1 Apr. 5, 2012

(51) Int. Cl.
*G01N 33/543* (2006.01)
*G01N 33/76* (2006.01)
*G01N 33/558* (2006.01)

(52) U.S. Cl.
CPC .......... *G01N 33/54386* (2013.01); *G01N 33/76* (2013.01); *G01N 33/558* (2013.01)
USPC ..................... 435/287.7; 435/287.9; 422/420; 422/425; 422/430; 436/518

(58) Field of Classification Search
None
See application file for complete search history.

(56) References Cited

U.S. PATENT DOCUMENTS

| 5,026,653 | A | * | 6/1991 | Lee et al. ...................... 436/518 |
| 5,602,040 | A | * | 2/1997 | May et al. ..................... 436/501 |
| 6,183,972 | B1 | * | 2/2001 | Kuo et al. ...................... 435/7.1 |
| 6,319,676 | B1 | | 11/2001 | Nazareth et al. |
| 6,767,714 | B2 | | 7/2004 | Nazareth et al. |
| 7,045,342 | B2 | | 5/2006 | Nazareth et al. |
| 2008/0213920 | A1 | * | 9/2008 | Nazareth et al. ............. 436/536 |
| 2010/0311188 | A1 | * | 12/2010 | Nazareth et al. ............. 436/501 |

* cited by examiner

*Primary Examiner* — Bao Thuy L Nguyen
*Assistant Examiner* — Rebecca Martinez
(74) *Attorney, Agent, or Firm* — Ryan Cagle

(57) ABSTRACT

The present invention is related to a diagnostic test kit for detecting luteinizing hormone (LH) in a biological sample at a concentration relative to a threshold concentration of LH. The device can include a release medium formed of a first material and including a labeled conjugate with a detectable label and a first binding member reactive with a first epitope of LH and a capture medium formed of a second, different material, in fluid communication with the release medium. The capture medium includes a result site having immobilized thereon a capture component capable of directly or indirectly binding LH that is bound to the labeled conjugate. The device is calibrated such that color development at the result site occurs only when the LH concentration of the liquid sample is greater than the threshold concentration.

20 Claims, 6 Drawing Sheets

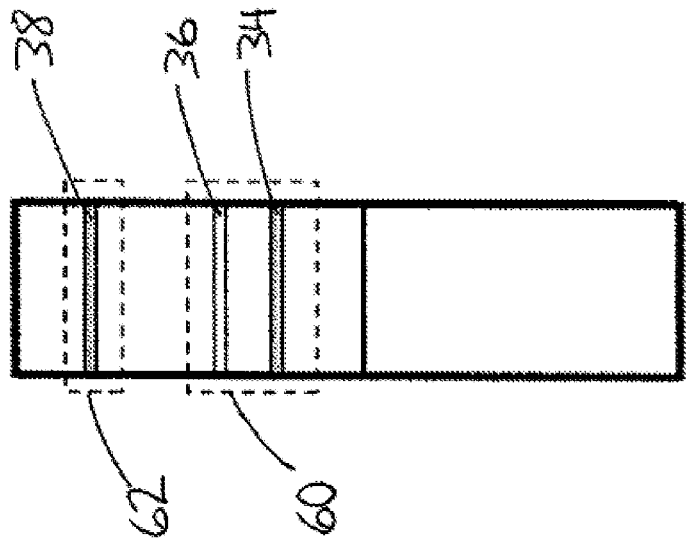
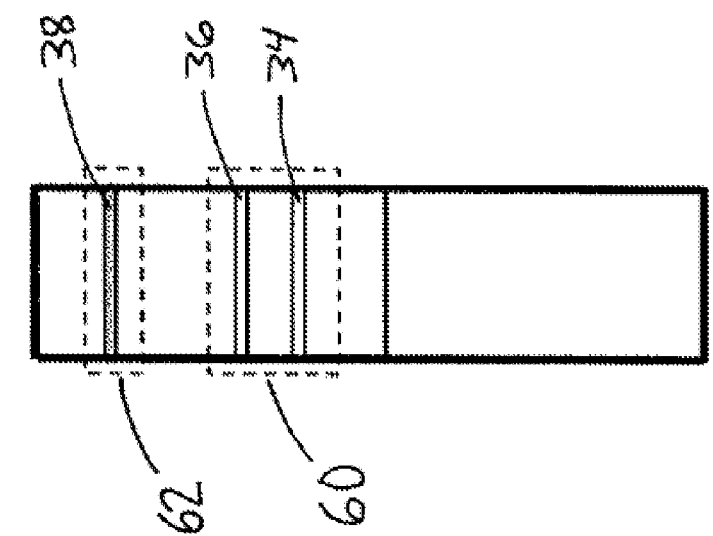
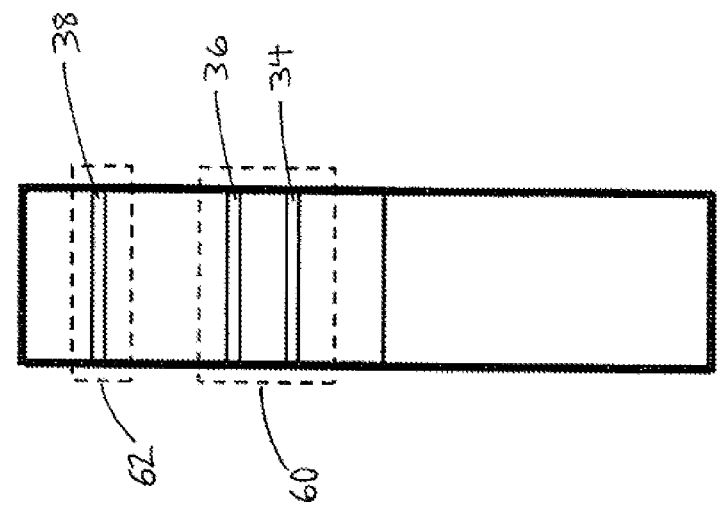

OVULATION PREDICTOR TEST

FIELD OF THE INVENTION

The present invention relates to methods and apparatus for detecting luteinizing hormone (LH) in a biological sample.

BACKGROUND OF THE INVENTION

Just prior to ovulation, women experience a short surge where the luteinizing hormone (LH) level rises to a significantly higher level relative to one's baseline, or normal circulating, LH level. As such, ovulation predictor tests are configured for the detection of this LH surge to facilitate the prediction of when a woman will ovulate. Generally, most women will ovulate within 24 to 36 hours after an LH surge is detected. A reliable method of predicting ovulation can determine a woman's fertility period for pregnancy. As such, ovulation predictor kits/devices must provide unambiguous test results (i.e., surge or no surge) to accurately facilitate the prediction of ovulation in a timely manner.

Ovulation predictor kits/devices currently available provide test results that can be difficult to interpret by a user due at least in part to the nature in which these test results are conveyed to the user. That is, ovulation predictor tests generally require the user to compare the resulting color intensities of the test line and reference line. In many instances, these devices are deemed to indicate LH surge when the test line exhibits a color intensity equal to or greater than the color intensity exhibited by the reference line. Accordingly, interpretation of these test results is necessarily subjective. For instance, as a user approaches the time of her LH surge the test results provided by these "color matching/comparing" devices become increasingly vague and subjective since the respective color intensities of the test and reference lines are increasingly similar. As such, the user is left to interpret as to whether the respective color intensities are truly indicative of an LH surge or not. This inherent guesswork can often result in the user missing the detection of her LH surge. The inability to timely identify an LH surge renders pinpointing ovulation undesirably difficult.

As such, there remains a need for a reliable ovulation predictor device that provides test results that can be less subjectively interpreted by a user, particularly by a user in her home.

SUMMARY OF THE INVENTION

The present invention provides a device for detecting the presence of an analyte in a biological sample comprising a release medium formed of a first material, wherein the release medium is configured to receive the biological sample, a capture medium located downstream from the release medium and in fluid communication with the release medium, the capture medium defining a result site, a scavenger binding member located on one of the release medium and the capture medium upstream from the result site, the scavenger binding member configured to directly or indirectly bind with a predetermined threshold concentration of the analyte, a labeled binding member reactive with a first epitope of the analyte to be detected in the biological sample, the labeled binding member being releasably disposed on the release medium and a second binding member capable of directly or indirectly binding to the analyte, the second binding member being disposed on one of the release medium and the capture medium, wherein detection of the analyte at the result site occurs only when the analyte concentration in the biological sample is greater than the predetermined threshold concentration.

In other embodiments, the second binding member is releasably placed on the release medium and reactive with a second epitope of the analyte, and a capture binding member is immobilized on the capture medium at the result site and is capable of directly or indirectly binding to one of the analyte and the second binding member. In some of these embodiments, the scavenger binding member is immobilized at a threshold site located upstream of the result site on the capture medium. In other of these embodiments, the scavenger binding member is the same as one of the capture binding member and the second binding member. In still other of these embodiments, the amount of the immobilized scavenger binding member at the threshold site is calibrated such that the analyte present in the biological sample exceeding the predetermined threshold concentration passes the threshold site and may be captured at the result site. In yet other of these embodiments, the analyte and the labeled first binding member are captured at both the threshold site and the result site.

In other embodiments, the analyte is Luteinizing Hormone (LH). In still other embodiments, a positive test result occurs when a visible line is present at the threshold site and the result site. In yet other embodiments, the device further comprises a case having at least one window formed therein, wherein the release medium and the capture medium are received in the case so that the result site and the threshold site align with the at least one window. In yet other embodiments, a combination of the labeled binding member, the second binding member and the analyte form a sandwich complex that is captured at least one of the threshold site and the result site.

In other embodiments, the detectable label is colloidal gold. In still other embodiments, the labeled binding member is an anti-LH antibody and the label is colloidal gold. In yet other embodiments, the second binding member is an anti-LH antibody. In further embodiments, the capture binding member further comprises at least one of polymerized streptavidin, streptavidin, neutravidin and avidin. In other embodiments, a control site is located on the capture medium, the control site having a control capture binding member that reacts with and binds to at least one of the labeled binding member and a control binding member. In yet other embodiments, the analyte is one of follicle-stimulating hormone (FSH), thyroid stimulating hormone (TSH) human chorionic gonadotrophin (HCG) and luteinizing hormone (LH).

In another preferred embodiment, a device for detecting an analyte in a biological sample comprises a casing having at least one window, a release medium received in the casing and adapted to receive a biological sample to be tested for the presence of the analyte, the release medium comprising a labeled binding member disposed thereon for binding with the analyte, a capture medium received in the casing and in fluid communication with the release medium, the capture medium defining a result site thereon, a second binding member disposed on one of the release medium and the capture medium and configured to directly or indirectly bind to one of the labeled binding member and the analyte, a scavenger binding member disposed on one of the release medium and the capture medium, the scavenger binding member configured to directly or indirectly bind to a predetermined threshold concentration of the analyte, wherein capture and detection of the analyte at the result site occurs when the overall concentration of the analyte in the biological sample is greater than the predetermined threshold concentration.

In some embodiments, the second binding member is releasably placed on the release medium and a capture binding member is immobilized at the result site. In other embodiments, the scavenger binding member is at least one of immobilized on the capture medium and releasably placed on the release medium. In other embodiments, the presence of the labeled binding member at the result site is a positive indication that the concentration of the analyte in the biological sample is greater than the predetermined threshold concentration.

In a preferred method in accordance with one embodiment of the present invention, a method of detecting the presence of an analyte over a predetermined threshold concentration in a biological sample, the method comprising the steps of receiving a biological sample on a test strip, binding of the analyte present in the biological sample to a labeled binding member, capturing a predetermined threshold concentration of the analyte such that any analyte in excess of the threshold concentration is available for detection, detecting analyte concentration in excess of the captured predetermined threshold concentration from step c in the biological sample, and presenting a visual indicator when the concentration of the analyte in the biological sample is greater than the predetermined threshold concentration.

In some embodiments, the step of presenting a visual indicator further comprises a color development occurring at a result site. In other embodiments, the analyte is luteinizing hormone (LH). In yet other embodiments, the label of the labeled binding member is colloidal gold. In still other embodiments, the step of capturing a predetermined threshold concentration of the analyte further comprises providing a binding member that captures the predetermined threshold concentration of the analyte.

BRIEF DESCRIPTION OF THE SEVERAL VIEWS OF THE DRAWINGS

A full and enabling disclosure of the present invention, including the best mode thereof directed to one of ordinary skill in the art, is set forth in the specification, which refers to the appended figures, in which:

FIGS. 4A-4E depict the biphasic substrate of FIG. 3B shown in various states of use and having a control window and a results window;

Figure 1A:
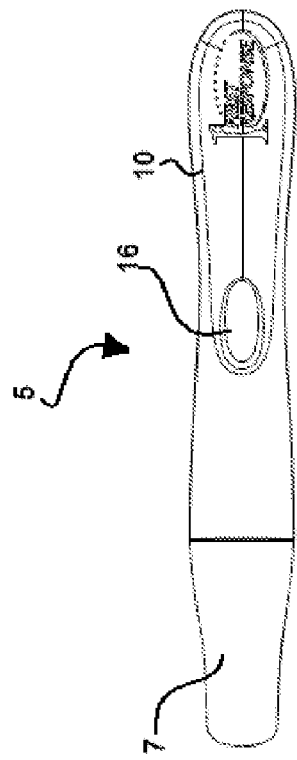
FIGS. 1A-1D illustrate a testing device in accordance with one embodiment of the present invention.
Figure 1C:
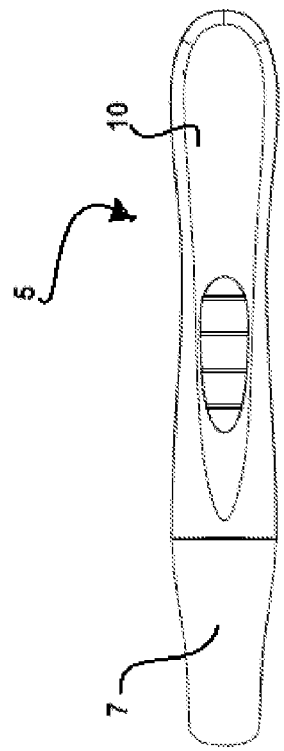
Figure 1B:
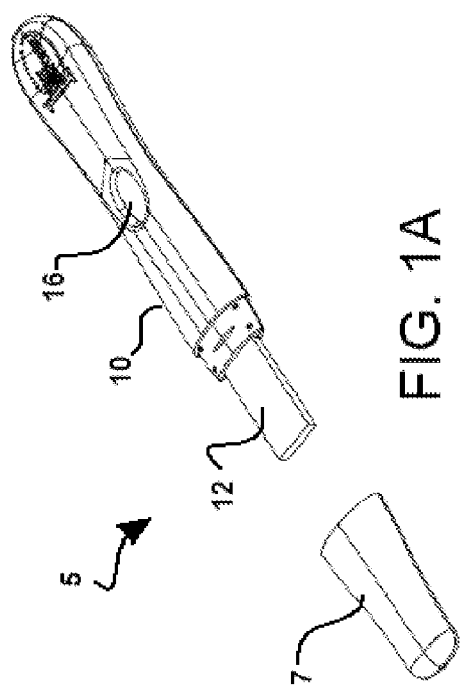
Figure 1D:
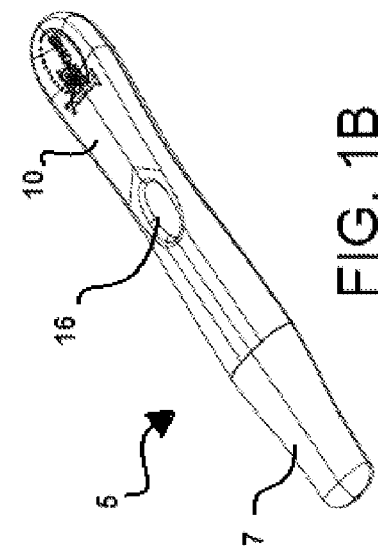

Repeat use of reference characters in the present specification and drawings is intended to represent same or analogous features or elements of the invention.

DETAILED DESCRIPTION OF THE INVENTION

The present invention now will be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. As used in the specification, the singular forms "a", "an", "the", include plural referents unless the context clearly dictates otherwise.

The term "biological sample," as used herein, refers to a sample of biological origin, or a sample derived from the sample of biological origin. The biological samples include, but are not limited to, blood, plasma, serum, saliva, cerebral spinal fluid, pleural fluid, milk, lymph, sputum, semen, urine, stool, tear, saliva, needle aspirate, external section of the skin, respiratory, intestinal, or genitourinary tract, tumor, organ, cell culture, cell culture constituent, tissue sample, tissue section, whole cell, cell constituent, cytospin, or cell smear.

As used herein, "antibody" refers to a polypeptide substantially encoded by an immunoglobulin gene or immunoglobulin genes, or fragments thereof, which recognizes and binds an antigen. The recognized immunoglobulin genes include the kappa, lambda, alpha, gamma, delta, epsilon, and mu constant region genes, as well as the immunoglobulin variable region genes. Antibodies include fragments, such as Fab', F(ab)2, Fabc, and Fv fragments. The term "antibody," as used herein, also includes antibody fragments either produced by the modification of whole antibodies or those synthesized de novo using recombinant DNA methodologies, and further includes "humanized" antibodies made by now conventional techniques.

As used herein, a "capture antibody" should be understood as an antibody, such as a monoclonal or polyclonal antibody, attached directly or indirectly to a substrate, such as a solid substrate. The capture antibody can include at least one binding member that recognizes and binds a particular, distinct epitope of an antigen, such as LH. Embodiments of the present invention preferably also make use of a conjugate (labeled binding member) comprising an antibody bound to a detectable label component (which can be colored particles, such as a metal sol or colloid, preferably gold).

Any detectable label recognized in the art as being useful in various assays could be used in the present invention. In particular, the detectable label component can include compositions detectable by spectroscopic, photochemical, biochemical, immunochemical, or chemical means. The label component thus produces a detectable signal. Exemplary labels include fluorescent dyes, chemiluminescent compounds, radioisotopes, electron-dense reagents, enzymes, or colored particles. The label component can generate a measurable signal, such as radioactivity, fluorescent light, color, or enzyme activity, which can be used to identify and quantify the amount of label bound to a test site. Thus, the label component can also represent the presence of a particular antigen bound thereto.

As used herein, an "analyte" refers to the material to be detected by use of the device and method of the present invention. "Analyte" includes but is not limited to: antigens, antibodies, hormones (such as FSH, TSH, Hcg, LH), drugs, proteins associated with a cell ("cell proteins"), secreted proteins, enzymes, cell surface or transmembrane proteins, glycoproteins and other proteins, peptides, and carbohydrates. Other analytes are described further throughout the specification.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In embodiments wherein the device of the invention makes use of a sandwich technique, the antibody used in the detection comprises a binding region or site which binds to an epitope on the analyte for detection, such as LH. The antibody designated as label antibody preferably has a label component bound thereto to form a labeled conjugate (labeled binding member), which reacts with the analyte of interest to form a complex in the liquid sample. The analyte bound to the conjugate (labeled binding member) reacts with a second antibody designated as capture antibody to form a "sandwich" of the capture antibody, analyte, and conjugate antibody (labeled binding member). In certain embodiments, a biotinylated capturable antibody can also be utilized. For example, the biotinylated capturable antibody can include a region or site that binds to a second epitope on the analyte. In these embodiments, the resulting "sandwich" comprises a complex of the labeled conjugate (labeled binding member)—analyte—biotinylated capturable antibody. In general, the "sandwich"complex is progressively produced as the biological sample with the analyte therein continuously moves along the test strip of the device. As more and more "sandwich" complex is immobilized at the capture site comprising of a binding member with affinity to the biotinylated capturable antibody, the label components aggregate and become visible through a viewing window, indicating the presence of a particular analyte in the biological sample.

Referring to FIGS. 1A-D, a schematic illustration of an embodiment of a test device 5 constructed in accordance with the present invention comprising an outer, molded casing 10 which defines a hollow, elongate enclosure. A removable cover 7 is secured to one end of casing 10 over a sample receiving material 12. Sample receiving material 12 is positioned so that part of the sample receiving material is received in the casing enclosure and part of the sample receiving material extends from the end of the casing. Casing 10 defines an opening 16 comprising a window through which a capture and a control site are visible. As illustrated in FIGS. 1A-D window 16 is disposed on one side of casing 10. It should be understood that the above description of a test device is for illustrative purposes, and other testing devices may be used. For example, the electronic testing device of U.S. Pat. No. 7,763,454, assigned to Church & Dwight Co. Inc., which is incorporated in its entirety by reference herein, is yet another example of a testing device in which the present invention may be used.

Figure 2A:
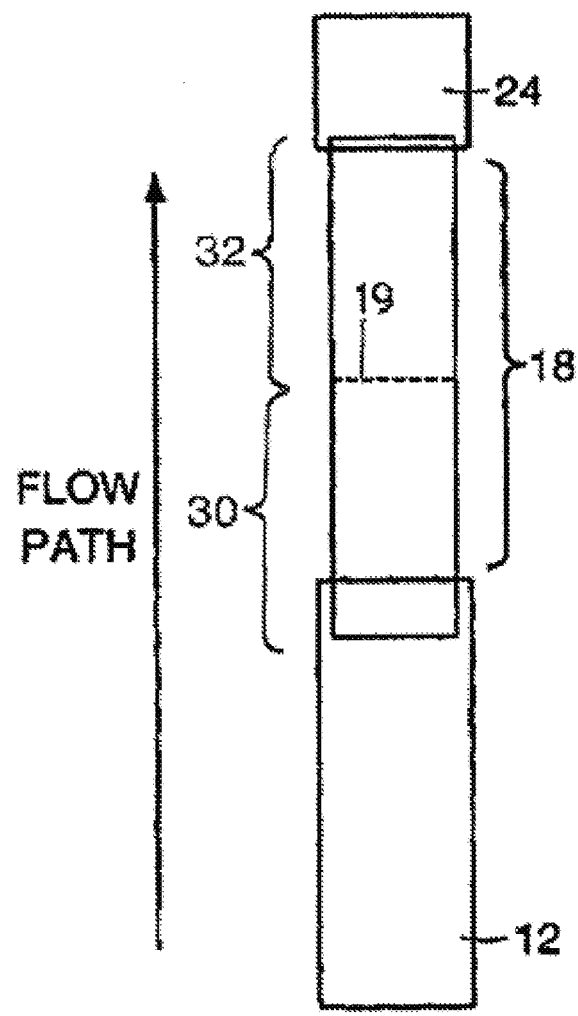
FIG. 2A depicts a schematic top view of an assay material according to one embodiment of the invention and for use in the testing device of FIG. 1.

Referring to FIG. 2A a preferred embodiment of an assay material comprises sample receiving material 12, a chromatographic substrate 18, and a reservoir absorbent material 24. The assay materials and the interior of the casing together define a flow path. A sample deposited on or adjacent the sample receiving material 12 is transported by capillary action, wicking, or simple wetting along the flow path downstream through the sample receiving material 12, along chromatographic substrate 18, and into reservoir absorbent material 24, generally as depicted by the arrow. The sample receiving material also serves as a filter which can remove from test samples particulate matter and interfering factors. The sample receiving material is preferentially disposed within the casing and extending to the exterior thereof.

In one preferred embodiment, sample receiving material 12 preferably is a bibulous hydrophilic material which facilitates absorption and transport of a fluid sample to chromatographic substrate 18. Such materials may include cellulose acetate, hydrophilic polyester, and other materials having similar properties. Further, a combination of absorbent materials also may be used. Non-limiting examples of useful materials include bonded cellulose acetate, bonded polyolefin, or hydrophilic polyester, such as those materials commercially available from Filtrona Fibertec Company (Colonial Heights, Va.). Other useful materials include absorbent matrices, such as Grade 939, Grade 989, Grade 1278, or Grade 1281, available from Ahlstrom Corporation. The sample application member preferably is coated with a buffered solution containing BSA and a nonionic surfactant, such as Triton X-100. The presence of BSA and surfactant minimize non-specific adsorption of the analyte. A concentration of about 1% BSA and about 0.2% surfactant in tris buffer can be effective for this purpose.

Still referring to FIG. 2A, in one preferred embodiment chromatographic substrate 18 is a biphasic chromatographic substrate 18, comprising a release medium 30 and a capture medium 32. Horizontal dashed line 19 represents the interface between release medium 30 and capture medium 32. The primary function of release medium 30 is first to support and to subsequently release and transport various immunological components of the assay, such as a labeled conjugate (labeled binding member) and/or a capturable component (formed from a second binding member), both of which can bind to the analyte of interest. This release and transport occurs during routine operation of the assay as described in detail herein. Generally, release medium 30 can be formed of any material capable of performing the function of holding, releasing, and transporting various immunological parts of the test such as the labeled conjugate (labeled binding member) and/or the capturable component (capturable binding member). Release medium 30 may be formed from a material which allows for release of indicator reagents.

In certain embodiments, release medium 30 comprises a bibulous, hydrophilic material, such as absorbent materials. Preferred materials for use as release medium 30 include, but are not limited to, cotton linter paper, such as S&S 903, S&S GB002, and BFC 180 (available from Whatman, Fairfield, N.J.); cellulosic materials or materials made of cellulose together with a polymeric fibrous material, such as Grade 939 made of cellulose with polyamide, Grade 989 made of cellulose blend fiber, and Grade 1278 and Grade 1281 made of cellulose and rayon with polyamide (available from Ahlstrom Corporation, Mt. Holly Springs, Pa.); and glass fiber, such as Lydall borosilicate (available from Lydall, Inc., Rochester, N.H.). The release medium preferably is coated with an aqueous solution containing bovine serum albumin (BSA) and a nonionic surfactant, such as Triton X-100 (available from Rohm & Haas Co., Philadelphia, Pa.) in order to prevent nonspecific binding and facilitate release of the diffusible reagents. A combination of about 3% BSA and about 0.1% Triton X-100 is useful for this purpose.

Capture medium 32 may be formed from a material that permits immobilization of reagents for detection of the presence of the analyte in the biological sample. Capture medium 32 generally comprises hydrophilic polymeric materials, such as microporous films or membranes that permit protein reagents to be immobilized directly on the membrane by passive adsorption without the need for chemical or physical fixation. Of course, the use of chemical or physical fixation is not precluded by the present invention, and any known method for immobilizing the reagents to the membrane can be used. Non-limiting examples of materials useful as capture medium 32 comprise a microporous polymeric film of nitrocellulose, nylon (e.g., nylon 66), or similar materials, or combinations of such materials.

Materials for use as capture medium 32 preferably have a pore size in the range of from about 5 μm to about 20 μm. In specific embodiments, the nitrocellulose membrane may be nitrocellulose alone or a mixed ester of nitrocellulose, such as in combination with an ester of nitric acid and/or other acids. The nitrocellulose membrane preferably is coated or laminated onto a translucent or transparent polymeric film to provide physical support for the membrane. In a preferred embodiment, a nitrocellulose polymer which has been cast onto a polyester film, such as MYLAR®, is used. Alternatively, a nitrocellulose membrane laminated onto a polyester film also may be used, although other backing materials besides polyester may be used. Pre-laminated or pre-cast sheets useful in the present invention are commercially available, for example, from Millipore Corporation, Bedford, Mass. And Sartorius Corporation, Edgewood, N.Y. Both media are in the form of planar strips, which are brought together to form a single flow path.

Figure 2B:
FIG. 2B depicts a schematic side view of the embodiment of the assay material of FIG. 2A.

Referring to FIG. 2B, a side view of one embodiment of the operative portion of the assay materials is shown where sample receiving material 12 is disposed proximate release medium 30, and overlaps release medium 30 at one end. Release medium 30 in turn overlaps capture medium 32, which is disposed distal to release medium 30. Again, release medium 30 and capture medium 32 may alternatively be connected via a butt joint rather than being in overlapping connection. Reservoir 24 overlaps a distal end of capture medium 32. These four components together form a single fluid path, and cooperate to cause sample liquid to flow from sample receiving material 12 along release medium 30 and capture medium 32 into reservoir 24. As previously noted, the interface of release medium 30 and capture medium 32 can be in the form of an overlapping relationship, or alternatively, release medium 30 can be butted up to capture medium 32. In one embodiment, the release medium and capture medium are brought together by overlapping the downstream edge of release medium 30 over the upstream edge of capture medium 32, then adhering the resulting biphasic material to a polymer film or sheet, thereby holding the media in place. The overlapping region allows for the efficient and rapid transfer of analyte containing biological sample from the release medium to the capture medium.

While the rapid transfer associated with the overlapping regions is useful, the manufacturing issues associated with reproducibly generating a small overlapping region, such as necessary with small devices, can be difficult. Therefore, in certain embodiments, the invention also provides a test device having a biphasic design as described herein but wherein release medium 30 and capture medium 32 do not overlap but rather are connected by a non-overlapping butt joint. In such embodiments, the fluid front moving along the test strip is transferred from the release medium to the capture medium through bridging the non-overlapping region by capillary action. Butt joining of the phases can maintain the same efficacy of the overlapping of the phases, even after accelerated aging of the devices. Thus, the use of a butt joint simplifies the manufacture of the present test device without any loss of performance in the device.

Disposed downstream of capture medium 32 is reservoir 24 comprising a relatively large mass of absorbent or superabsorbent material. The purpose of reservoir 24 is generally to ensure that a reasonably large amount of biological sample is drawn across the chromatographic medium. In certain embodiments, sample receiving material 12 can be omitted, and release medium 30 can itself act as the sample receiving material. Such embodiments of the assay materials are useful in performing dipstick assays. By providing reservoir absorbent material 24 disposed beyond chromatographic substrate 18, a relatively large volume of the test liquid and any analyte it contains can be drawn through the test area to aid in background clearance and enhance sensitivity. Reservoir absorbent material 24 preferably comprises a hydrophilic material which may be the same as upstream sample receiving material 12. Reservoir absorbent material 24 generally facilitates capillary action along chromatographic substrate 18 and absorbs excess liquid contained within device 5. Reservoir absorbent material preferably compromises absorbent paper made from cotton linter fibers, such as CF3, CF4, CF5 or 470 (available from Whatman) or cellulosic materials, such as Grade 3MM (available from Whatman) and Grade 320 (available from Ahlstrom). It should be understood that not all embodiments of the present invention will use reservoir 24 and may implement various other methods for dealing with excess fluid sample.

Figure 3A:
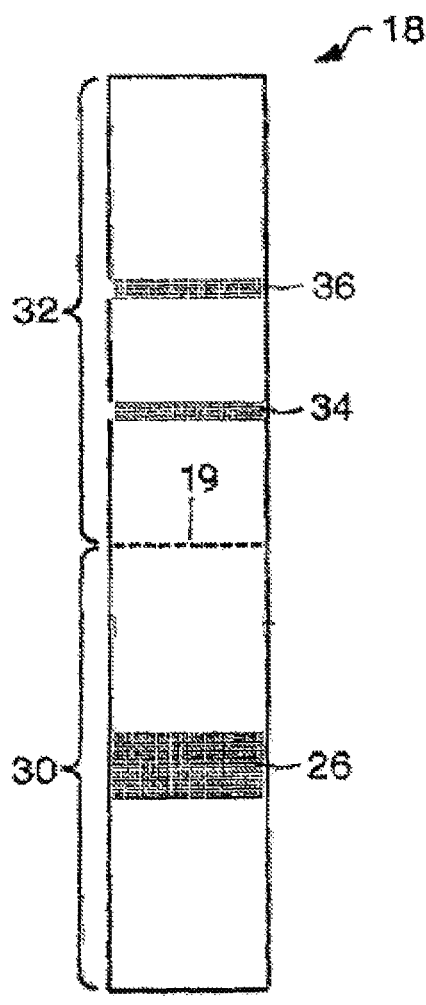
FIG. 3A depicts a schematic top view of a biphasic substrate according to another embodiment of the present invention for use in the assay material of FIG. 2A and the testing device of FIG. 1.

Referring to FIG. 3A, a band 26 formed from a labeled conjugate (labeled binding member), e.g., an antibody-metal sol is deposited on release medium 30 downstream from sample receiving material 12. Band 26 includes a labeled binding member reactive with a particular site (sometimes referred to as a "first epitope") on the analyte of interest. The labeled binding member further comprises a detectable label, preferably colloidal gold. In certain embodiments, the label component preferably comprises a gold colloid having a mean particle size of about 50 nm to about 100 nm prior to formation of the labeled conjugate More preferably, the mean particle size can range from about 60 nm to about 80 nm prior to formation of the labeled conjugate. Such label components particularly are described in U.S. Pat. No. 7,776,618, which is incorporated herein by reference in its entirety.

Figure 3B:
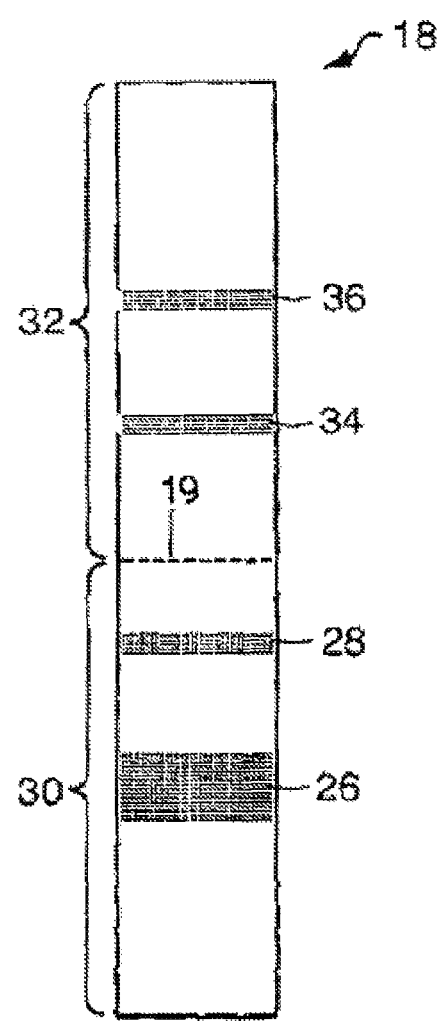
FIG. 3B depicts a schematic top view of a biphasic substrate according to another embodiment of the present invention for use in assay material of FIG. 2A and the testing device of FIG. 1.

Referring to FIG. 3B, a second band 28 of capturable component having a capturable binding member, e.g., antibody-biotin is located on release medium 30 downstream of band 26, and is reactive with another particular site (sometimes referred to as a "second epitope") on the analyte of interest. The first epitope and the second epitope are preferably different sites on the analyte. In one embodiment, both the labeled binding member and the capturable binding member are in dehydrated form. The capturable binding member comprises one member of an affinity pair and is capable of forming a sandwich complex with the labeled binding member and the analyte. The labeled binding member and the capturable binding member both are releasably bound to release medium 30 such that when the fluid front created by the biological sample being analyzed passes through release medium 30, band 26 and band 28, both the labeled binding member and the capturable binding member become mobilized by the liquid and flow with the fluid front along the liquid path. In operation, if any analyte is present in the biological sample, it preferably reacts first with the labeled binding member, then with the capturable binding member as the fluid front advances along the liquid path to form a diffusible sandwich which is transported by capillary action to capture medium 32.

Still referring to FIGS. 3A-3B, immobilized on capture medium 32 are, respectively, a threshold site 34 having a scavenger binding member and a result site 36 having capture binding member (a capture component), which generally comprise the other member of the affinity pair specific for the capturable component. For example, upon diffusion into capture medium 32, the diffusible sandwich becomes concentrated by the interaction of the binding member (the capturable affinity) with the scavenger binding member (the capture affinity) at threshold site 34 so as to capture the capturable sandwich complex as it moves across threshold site 34. Threshold site 34 is calibrated to capture either directly or indirectly a threshold concentration of analyte of interest such that any analyte of interest in excess of the threshold concentration is available for binding at result site 36. Depending on the use of the testing device, the scavenger binding member and capture binding member may be the same or different.

The scavenger binding member is immobilized at threshold site 34, preferably by simple adsorption and does not advance with the fluid front. Once the threshold concentration of analyte has been met, any excess analyte moves with the fluid front toward result site 36, where it is immobilized by the capture binding member similar to that of threshold site 34. In FIGS. 3A-3B, threshold and result sites 34 and 36 are illustrated as being disposed serially along the flow path. Alternatively, the sites may be disposed in other spatial relationships. The invention is not limited by the precise nature of sites 34 and 36. Antibody or other affinity agents can be immobilized at sites 34 and 36 using absorption, adsorption, or ionic or covalent coupling, in accordance with methods known per se. Capture medium 32 preferably is selected to bind the capture reagents without the need for chemical coupling. Nitrocellulose and nylon both permit non-chemical binding of the capture component and control reagent. In one preferred embodiment, the diffusible reagents at bands 26 and 28 and non-diffusible reagents at threshold site 34 and result site 36 are applied to the release and capture media, respectively, by direct application onto the surface of the medium and dried to form a narrow band. The non-diffusible reagents preferably are applied to the capture medium by passive adsorption.

In operation, a liquid sample is applied to sample receiving material 12, which is in contact with a proximal end of biphasic chromatographic substrate 18. Casing 10 of device 5 may be configured to permit direct contact with a fluid sample as described above or sample receiving material 12 may be used as a dipstick for dipping in a container of the fluid or test sample. The liquid sample travels, impelled by surface effects such as by capillary action, along a liquid path formed by biphasic chromatographic substrate 18. More specifically, the test sample passes through release medium 30 through labeled binding member band 26 and capturable binding member band 28, which are 13 reconstituted in the fluid front. If the analyte of interest is present in the sample, it sequentially reacts with the labeled binding member and the capturable binding member, thereby forming a capturable sandwich complex. Once formed the sandwich complex comprising the analyte, labeled binding member and the capturable binding member travels along capture medium 32 and reacts with the immobilized scavenger binding member at threshold site 34, the scavenger binding member being specific for the affinity agent on the capturable binding member. This process results in the capturable sandwich complex accumulating at the threshold site. If the amount of capturable sandwich complex exceeds a predetermined concentration threshold, the additional capturable sandwich complex moves towards and accumulates at result site 36 by binding with the immobilized capture binding member. Depending on the use of the testing device, the scavenger binding member at threshold site 34 and capture binding member at result site 36 may be the same or different. The presence of the analyte above a predetermined threshold level is determined by observing the presence of the detectable label at threshold site 34 and result site 36. If either no analyte is present in the sample or the level of the analyte is less than the predetermined threshold concentration, no detectable label will be present at the result site but may be present at the threshold site. If, on the other hand, a sufficient concentration of analyte is present in the biological sample, then labeled sandwich complex will be captured at both the threshold site and the result site causing two lines to develop. Thus, a positive result occurs when color is detectable at both the result site and the threshold site regardless of the intensity of the color.

In another preferred embodiment, a band 26 formed from a labeled conjugate (labeled binding member), e.g., an antibody-metal sol is deposited on release medium 30 downstream from sample receiving material 12. Band 26 includes a binding member reactive with a particular site (sometimes referred to as a "first epitope") on the analyte of interest. The labeled binding member further comprises a detectable label, preferably colloidal gold. In certain embodiments, the label component preferably comprises a gold colloid having a mean particle size of about 50 nm to about 100 nm prior to formation of the labeled conjugate More preferably, the mean particle size can range from about 60 nm to about 80 nm prior to formation of the labeled conjugate. Immobilized on capture medium 32 are, respectively, a threshold site 34 having a scavenger binding member and a result site 36 having capturable binding member, e.g., antibody is located at result site 36, and is reactive with another particular site (sometimes referred to as a "second epitope") on the analyte of interest. The first epitope and the second epitope are preferably different sites on the analyte, which generally comprise the other member of the affinity pair specific for the capturable component. Depending on the use of the testing device, the scavenger binding member and capture binding member may be the same or different. Thus, upon diffusion into capture medium 32, the diffusible half-sandwich complex comprising the analyte and the labeled binding member becomes concentrated by the interaction of the analyte with the scavenger binding member at threshold site 34 so as to capture the half-sandwich complex as it moves across threshold site 34 thereby completing the sandwich complex. Threshold site 34 is calibrated to capture a threshold concentration of analyte of interest such that any analyte of interest in excess of the threshold concentration is available so as to capture any excess half-sandwich at result site 36. As with the previous preferred embodiment, if sufficient analyte is present above the predetermined threshold value, half-sandwich complex will be present at both the threshold site and the result site.

Figure 4E:
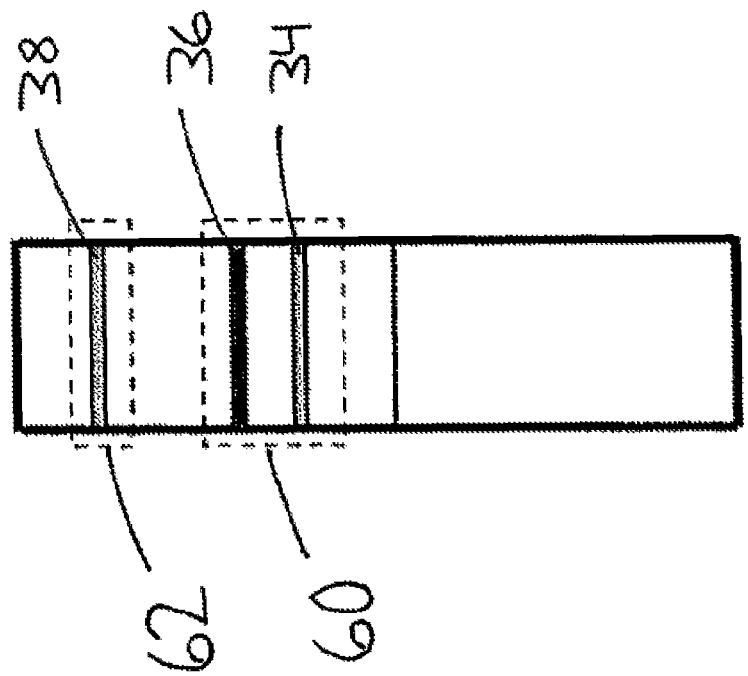

Referring to FIGS. 4A-4C, regardless of whether sandwich formation occurs during wicking of the fluid front or at the respective sites (e.g., regardless of format employed), capture medium 32 should also contain a control site 38 positioned separate from threshold site 34 and result site 36. In such embodiments, release medium 30 can include a labeled control member comprising a detectable label and an antibody that is not reactive with the analyte of interest. Control site 38 has immobilized thereon a capture component (control capture binding member) that is reactive with the labeled control member. Accordingly, the labeled control member will travel along the fluid front of the biological sample and ultimately bind with the control capture binding member immobilized at control site 38. Preferably, control site 38 is located downstream of both threshold site 34 and result site 36. Detection (by color development) of the labeled control member at control site 38 informs a user that the biological sample has in fact traveled downstream and reconstituted the labeled binding components.

In yet another embodiment, which is particularly useful when the diagnostic device comprises a biphasic test strip medium, the biphasic medium comprises a control site disposed on the capture medium downstream of the capture site. The control site has immobilized thereon an agent capable of capturing the labeling antibody. The primary function of the control site is to capture and immobilize antibody which has not been captured at the capture site. In a preferred embodiment, the control site has immobilized thereon polyclonal antisera specific for the labeling antibody. Indication of the presence of the label component at the control site indicates proper functioning of the test, irrespective of the presence or absence of analyte in the sample In one preferred embodiment, the labeled control binding member can comprise an antibody derived from a species different than the labeled binding member for the assay of interest. The labeled control member can be added to release medium 30 with and at the same location as the labeled binding member. By way of example only, the labeled binding member can be mouse derived and the labeled control member can be sheep derived. Furthermore, control capture binding member immobilized at control site 38 specifically recognizes the antibody of the labeled control member. For instance, if the antibody of the labeled control member is derived from sheep, the control capture binding member at control site 38 would be anti-sheep IgG antibody.

In one preferred embodiment, device 5 is configured to detect LH in a biological sample at a concentration relative to a threshold value. Release medium 30 includes a labeled binding member comprising colloidal gold and an antibody reactive with a first epitope of LH. A biotinylated capturable binding member reactive with a second epitope of LH is also disposed on release medium 30 downstream from band 26. In the presence of LH in the sample, a capturable sandwich complex is formed comprising the labeled binding member, LH, and the biotinylated capturable binding member. Capture medium 32 comprises a threshold site and a result site having immobilized thereon a capture binding member formed from streptavidin, polymerized streptavidin, neutravidin, or combination thereof capable of directly or indirectly binding LH that is bound to the labeled binding member. In one embodiment, the capture binding member at threshold site 34 and result site 36 comprises polymerized streptavidin, more preferably greater than 50% by weight of the polymerized streptavidin is at least about 100 kDa in size.

Threshold site 34 is calibrated such that color development at result site 36 occurs only when a concentration of LH of the liquid sample is greater than a threshold concentration determined by threshold site 34. Thus, once the capture binding member at threshold site 34 is saturated, the capturable sandwich complex reacts with the capture binding member at result site 36 causing the sandwich complex to remain at result site 36. That is, the threshold site is calibrated to bind only an amount of LH up to the defined LH surge threshold. When LH is present in the liquid sample at a concentration greater than the threshold concentration, excess LH in the sample passes the threshold site and moves toward the result site. At least a portion of the excess LH that passes the threshold site is bound at the result site. As such, color development occurs at the threshold site and the result site. According to these embodiments, the test results are read by the user in a manner similar to that of a traditional pregnancy test rather than by the subjective color matching means of other ovulation predictor tests. That is, indication of an LH surge is indicated by color development at both the threshold site and the result site (regardless of respective color intensities). Preferably, at least threshold site 34 and result site 36 is visible to a user, such as through window 16 (FIGS. 1A-1E) in the device's exterior casing 10.

Accordingly, analyte testing device 5 provides a quick, non-intrusive, and convenient means for determining if a user has reached a surge in LH by simply counting the number of colored lines in a results window of a device. Desirably, relative color intensities of the test sites do not impact the interpretation of the results provided by the test device. Furthermore, a user can also establish that the particular test device is functioning by simply viewing a resulting color development at the control site.

Referring to FIG. 4A, an unused device according to one embodiment of the invention is shown having a result window 60 and a control window 62. Since the device has yet to be used, neither of threshold site 34, result site 36, nor control site 38 exhibit any color development. Referring to FIG. 4B, a test result in which only control site 38 has exhibited an identifiable color development is shown. As such, these results quickly inform a user that the biological sample did not include a surge level of LH and also that this particular device is functional. That is, the color development at the control site informs the user that the fluid sample passed through the length of the device and therefore reconstituted the labeled binding member. Similarly, FIG. 4C illustrates test results indicating that the sample did not include a surge level or concentration of LH sufficient to bind at result site 36. In particular, threshold site 34 exhibits color development but result site 36 has not exhibited any color development. As such, the biological sample included LH but the concentration of LH in the sample was less than the threshold concentration indicative of a surge in LH. Additionally, the color development at control site 38 confirms to the user that the biological sample passed over the result site.

Figure 4D:
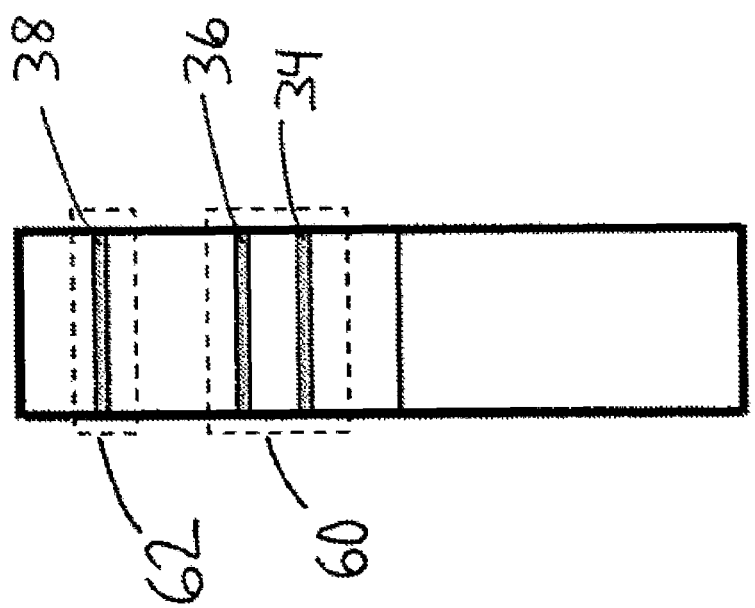

Referring to FIG. 4D, a test result indicates that the biological sample contained a concentration of LH deemed high enough to constitute a surge in LH. In particular, a user interpreting these results can see color development at threshold site 34 and result site 36 through result window 60. Since color development is observed at result site 36, the biological sample contained enough LH to be considered as an LH surge. As viewed through control window 62, the observed color development at control site 38 informs the user that the test device was functional. Finally, referring to FIG. 4E, a test result in which the color development at result site 36 is darker than the color development at threshold site 34. These results are indicative of LH surge. As described previously, the relative color intensities of the sites is not a factor in assessing LH surge using devices according to embodiments of the present invention. For instance, if the color intensity of the result site is faint as compared to the color intensity of the threshold site, then these results are also indicative of LH surge. In other embodiments not illustrated in the figures, the threshold site, result site and control site can be located in a single window.

While the assessment of LH surge in either the traditional or avidin-biotin lateral flow assay allows the direct or indirect capture of LH or LH complex, alternative methods can be employed to determine the presence of LH above a threshold concentration level through the use of a monoclonal or polyclonal scavenger antibody or a combination of avidin and polymerized streptavidin. Such embodiments generally include a scavenger site(s), either in solution or immobilized upstream to the result window, that is capable of capturing LH, a labeled antibody-LH complex, biotinylated antibody-LH complex, labeled antibody-LH-antibody sandwich, or a labeled antibody-LH-biotinylated antibody sandwich. In practical terms, similar to the visible threshold scavenger site discussed above, this serves to 'subtract' a threshold concentration of LH present within the sample prior to reaching the result site, effectively removing that LH from the sample as it flows down the test strip, either in solution or by directly or indirectly immobilizing the LH prior to the result window. One advantage of this scavenger format over a threshold line format is that it allows a preset amount of LH to be subtracted from the sample (i.e., levels of LH equivalent to the threshold concentration level) therefore only allowing LH levels above the threshold concentration level to be captured at the result site. This scavenger format allows an even simpler display of test results, with the results conveyed by either two lines (result site and control site) or one line (control site). Since the threshold concentration level of the assay is controlled by the scavenger binding member design, this one line/two line test result interpretation will be similar to the current pregnancy tests in which the detection of a labeled conjugate sandwich complex at the result site indicates a concentration of LH in the sample deemed to constitute an LH surge. For example, when LH is present in levels equivalent to or above the threshold concentration level, the color developed at the result site and control site informs the user that she has reached a surge in LH via a two line result. On the other hand, when no discernible color is present at the result site, the LH level would be deemed as "non-surge" via a one line result. In this way, the results obtained while using a scavenger binding member are similar in nature to pregnancy test kit without the need to subjectively evaluate relative color intensities.

Figure 5:
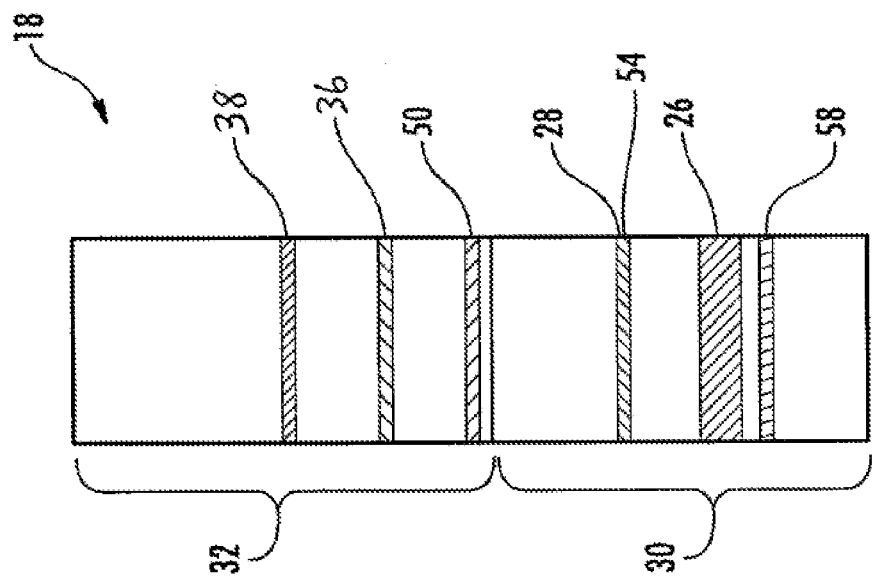
FIG. 5 depicts a schematic top view of a biphasic substrate according to another embodiment of the present invention having a scavenger component according to certain embodiments of the present invention.

Referring to FIG. 5, a biphasic chromatographic substrate 18 is shown including a release medium 30 and a capture medium 32. As described above with respect to FIGS. 3A-3B, release medium 30 includes a band 26 of labeled binding member, e.g., an antibody-metal sol, and a band 28 of capturable binding member e.g., antibody-biotin, releasably disposed on release medium 30. Immobilized on capture medium 32 are, respectively, a result site 36 and a control site 38 similar to that described with respect to FIGS. 3A-3B. Also striped on capture medium 32 is band 50 of scavenger binding member optionally located upstream of result site 36 and control site 38. A band 54 of scavenger binding member may also be striped in the same band as capturable binding member 28. Finally, a band 58 of scavenger binding member can be striped upstream of labeled binding member band 26. It should be understood that one or more bands of scavenger binding members, i.e. bands 50, 54 and 58, may be used in the testing device of FIG. 5 in either a mobilized or immobilized form.

In certain of the above embodiments, at least one of said bands 50, 54 and 58 and threshold site 34 is reactive with any of the following: (i) LH, (ii) a complex comprising of LH that is bound to a labeled binding member, (iii) a complex comprising of LH that is bound to a biotinylated capturable binding member (iv) a sandwich complex comprising of biotinylated capturable binding member with LH that is bound to a labeled binding member, or (v) combinations of (i) through (iv). For example, a device for detecting LH surge can include a release medium formed of a first material and comprising a detectable label and a capture medium in fluid communication with the release medium and formed of a second, different material, the capture medium comprising a result site. Such an embodiment also includes at least one of said bands 50, 54 and 58 and threshold site 34 that is reactive with any of the following: (i) LH, (ii) a complex comprising of LH that is bound to a labeled binding member, (iii) a complex comprising of LH that is bound to a biotinylated capturable binding member (iv) a sandwich complex comprising of biotinylated capturable binding member with LH that is bound to a labeled binding member, or (v) combinations of (i) through (iv). Accordingly, at least one of said bands 50, 54 and 58 and threshold site 34 binds low levels (i.e., less than and up to including the threshold amount of LH) of LH that are in a biotinylated capturable binding member-LH-labeled binding member complex, preventing these complexes from reaching the result line. The at least one of said bands 50, 54 and 58 and threshold site 34 can be located between the location of sample receiving material and the result site, and can essentially 'subtract' the threshold level of LH in either liquid phase or through immobilizing it on the capture medium. In the above described embodiment, the at least one of said bands 50, 54 and 58 is located between the sample receiving material and the result site and is provided in an amount sufficient to bind with a threshold concentration of LH, so that any excess LH above the threshold concentration in the sample will be bound to the labeled binding member and detected at the result site. A positive determination of LH surge in these embodiments is established by the detection of any color development at the result site. That is, color development at the result site indicates that the sample includes an LH surge concentration. Absence of color development at the result site indicates that the sample did not include an LH surge concentration.

The devices and methods described herein provide a less subjective means for a user to identify the day in their cycle in which they experience a surge in LH. As such, the devices and methods described herein also provide methods for predicting ovulation. For instance, most women generally will ovulate within 24 to 36 hours after an LH surge is detected. As such, upon detection of LH surge according to embodiments of the present invention, a user can easily predict her window of ovulation as generally occurring from 24 to 36 hours after the time of the urine assay (assuming the urine sample is immediately assayed after urination).

EXAMPLES

Figure 6:
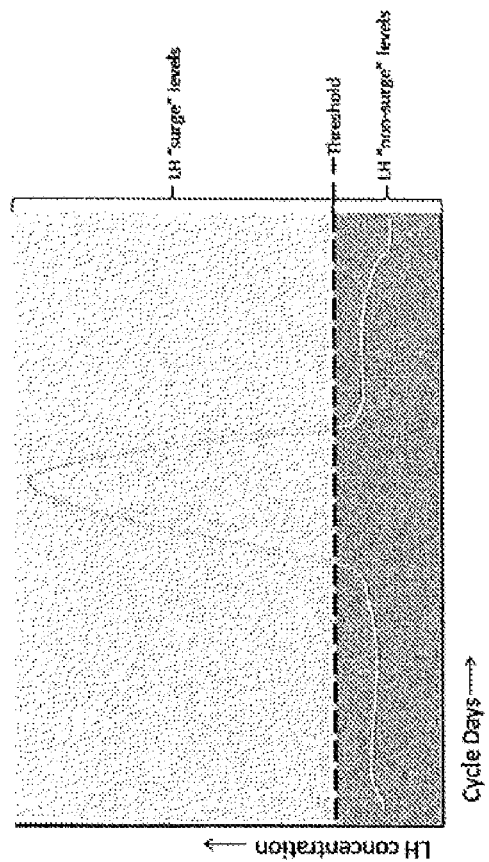
FIG. 6 depicts one particular threshold line calibration.

Test devices were produced with a biphasic medium containing Millipore 90 nitrocellulose (capture medium) and Ahlstrom 989 (release medium). The biphasic mediums were each striped with reagents as discussed herein. The threshold site was calibrated to ensure that it reached saturation (maximum binding) of antibody sandwiches at a LH concentration equivalent to the immunoreactivity represented by 40 Miu of the LH standard (WHO $2^{nd}$ IS, 80/552), such that the concentration is deemed adequate as constituting an LH surge. For example, FIG. 6 generally illustrates one threshold site calibration. Once saturation of the threshold site is reached, additional antigen-antibody sandwiches are free to flow past the threshold site and bind at the result line, conveying an LH surge result to the user. Each biphasic medium was provided with the following: (i) a threshold site striped at 1.35 mg/Ml (polymerized streptavidin); (ii) a result site striped at 2.25 mg/Ml (polymerized streptavidin); and (iii) a control site striped at 1.0 mg/Ml (control antibody). The test devices were tested against urine samples obtained daily from four subjects over the course of one non-conceptive cycle. For comparison, the urine samples were characterized for LH content utilizing a Siemens Immulite 1000 analyzer validated for quantitative LH measurements in urine.

Results obtained by the test devices were recorded as indicated in Tables 1-4 below. A determination of no LH surge in a urine sample (i.e., non-surge) was recorded when color development was only observed at (i) the control site or (ii) the control site and the threshold site. A determination of an LH surge in a urine sample (i.e., surge) was recorded when color development was observed at all of the following: (i) the control site; (ii) the threshold site; and (iii) the result site. As such, the detection and determination of surge levels of LH was based on line counting.

TABLE 1

| Subject Code # | Sample Date | Day of Cycle | LH (mIU/Ml) | MP90/1.35 ISA (Surge/NonSurge) |
|---|---|---|---|---|
| KOKKA | Feb. 5, 2008 | 4 | 8 | Not Tested |
| | Feb. 6, 2008 | 5 | 12 | Not Tested |
| | Feb. 7, 2008 | 6 | 7 | Not Tested |
| | Feb. 8, 2008 | 7 | 5 | Not Tested |
| | Feb. 9, 2008 | 8 | 4 | Non-Surge |
| | Feb. 10, 2008 | 9 | 9 | Non-Surge |
| | Feb. 11, 2008 | 10 | 7 | Non-Surge |
| | Feb. 12, 2008 | 11 | 17 | Non-Surge |
| | Feb. 13, 2008 | 12 | 132 | Surge |
| | Feb. 14, 2008 | 13 | 75 | Surge |
| | Feb. 15, 2008 | 14 | >200 | Surge |

TABLE 2

| Subject Code # | Sample Date | Day of Cycle | LH (mIU/Ml) | MP90/1.35 ISA (Surge/NonSurge) |
|---|---|---|---|---|
| CLIMA | Jan. 9, 2008 | 4 | 14 | Not Tested |
| | Jan. 10, 2008 | 5 | 17 | Not Tested |
| | Jan. 11, 2008 | 6 | 16 | Not Tested |
| | Jan. 12, 2008 | 7 | 11 | Not Tested |
| | Jan. 13, 2008 | 8 | 11 | Not Tested |
| | Jan. 14, 2008 | 9 | 36 | Not Tested |
| | Jan. 15, 2008 | 10 | 10 | Not Tested |
| | Jan. 17, 2008 | 12 | 19 | Non-Surge |
| | Jan. 18, 2008 | 13 | 45 | Non-Surge |
| | Jan. 19, 2008 | 14 | 15 | Non-Surge |
| | Jan. 20, 2008 | 15 | 15 | Non-Surge |
| | Jan. 21, 2008 | 16 | 14 | Non-Surge |
| | Jan. 22, 2008 | 17 | 25 | Non-Surge |
| | Jan. 23, 2008 | 18 | >200 | Surge |

TABLE 3

| Subject Code # | Sample Date | Day of Cycle | LH (mIU/Ml) | MP90/1.35 ISA (Surge/NonSurge) |
|---|---|---|---|---|
| HARDE | Jan. 4, 2008 | 5 | 22 | Not Tested |
| | Jan. 5, 2008 | 6 | 38 | Not Tested |
| | Jan. 6, 2008 | 7 | 28 | Not Tested |
| | Jan. 7, 2008 | 8 | 32 | Not Tested |
| | Jan. 9, 2008 | 10 | 31 | Non-Surge |
| | Jan. 10, 2008 | 11 | 44 | Non-Surge |
| | Jan. 11, 2008 | 12 | 88 | Surge |
| | Jan. 12, 2008 | 13 | >200 | Surge |
| | Jan. 13, 2008 | 14 | >200 | Surge |

TABLE 4

| Subject Code # | Sample Date | Day of Cycle | LH (mIU/Ml) | MP90/1.35 ISA (Surge/NonSurge) |
|---|---|---|---|---|
| KERBA | Jan. 12, 2008 | 4 | 13 | Not Tested |
| | Jan. 13, 2008 | 5 | 11 | Not Tested |
| | Jan. 14, 2008 | 6 | 18 | Not Tested |
| | Jan. 15, 2008 | 7 | 12 | Non-Surge |
| | Jan. 16, 2008 | 8 | 10 | Non-Surge |
| | Jan. 17, 2008 | 9 | 10 | Non-Surge |
| | Jan. 18, 2008 | 10 | 17 | Non-Surge |
| | Jan. 19, 2008 | 11 | 50 | Surge |
| | Jan. 20, 2008 | 12 | 116 | Surge |
| | Jan. 21, 2008 | 13 | 108 | Surge |

As illustrated by the results summarized in Tables 1-4 above, the test devices (tested against clinical urine samples) can discriminate LH concentrations indicative of a non-surge from those indicative of a surge as evident by agreement with the independent evaluations made with the Siemens Immulite 1000 analyzer. The threshold site was calibrated to ensure that it reached saturation (maximum binding) of antibody sandwiches at a LH concentration equivalent to the immunoreactivity represented by 40 Miu of the LH standard (WHO $2^{nd}$ IS, 80/552), such that the concentration was representative of an LH surge in clinical urine samples.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole and in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein. Although specific terms are employed herein, they are used in a generic and descriptive sense only and not for purposes of limitation.

We claim:

1. A device for detecting the presence of an analyte in a biological sample comprising:
   a. a release medium formed of a first material, wherein said release medium is configured to receive the biological sample;
   b. a capture medium located downstream from said release medium and in fluid communication with said release medium;
   c. a result site located on said capture medium;
   d. a scavenger binding member located on one of said release medium and said capture medium upstream from and separate from said result site, said scavenger binding member configured to directly or indirectly bind with a predetermined threshold concentration of the analyte;
   e. a labeled binding member reactive with a first epitope of the analyte to be detected in the biological sample, said labeled binding member being releasably disposed on said release medium;
   f. a second binding member capable of directly or indirectly binding to said analyte, said second binding member being disposed on one of said release medium and said capture medium; and
   g. a capture binding member is immobilized on said capture medium at said result site and is capable of directly or indirectly binding to one of said analyte and said second binding member, wherein detection of the analyte at said result site occurs only when the analyte concentration in the biological sample is greater than said predetermined threshold concentration.

2. The device of claim 1, wherein said second binding member is releasably placed on said release medium and reactive with a second epitope of the analyte.

3. The device of claim 2, wherein said scavenger binding member is immobilized at a threshold site located upstream from and separate from said result site on said capture medium.

4. The device of claim 2, wherein said scavenger binding member is the same as one of said capture binding member and said second binding member.

5. The device of claim 3, wherein the amount of said immobilized scavenger binding member at said threshold site is calibrated such that the analyte present in the biological sample exceeding said predetermined threshold concentration passes said threshold site and may be captured at said result site.

6. The device of claim 3, wherein the analyte and said labeled first binding member are captured at both said threshold site and said result site.

7. The device of claim 1, wherein said analyte is Luteinizing Hormone (LH).

8. The device of claim 3, wherein a positive test result occurs when a visible line is present at said threshold site and said result site.

9. The device of claim 3, wherein said device further comprises a case having at least one window formed therein, wherein said release medium and said capture medium are received in said case so that said result site and said threshold site align with said at least one window.

10. The device of claim 2, wherein a combination of said labeled binding member, said second binding member and said analyte form a sandwich complex that is captured at least one of said threshold site and said result site.

11. The device of claim 1, wherein said detectable label is colloidal gold.

12. The device of claim 1, wherein said labeled binding member is an anti-LH antibody and said label is colloidal gold.

13. The device of claim 1, wherein said second binding member is an anti-LH antibody.

14. The device of claim 2, wherein said capture binding member further comprises at least one of polymerized streptavidin, streptavidin, neutravidin and avidin.

15. The device of claim 1 further comprising a control site located on said capture medium, said control site having a control capture binding member that reacts with and binds to at least one of said labeled binding member and a control binding member.

16. The device of claim 1, wherein the analyte is one of follicle-stimulating hormone (FSH), thyroid stimulating hormone (TSH) human chorionic gonadotropin (HCG) and luteinizing hormone (LH).

17. A device for detecting an analyte in a biological sample comprising:
   a. a casing having at least one window;
   b. a release medium received in said casing and adapted to receive a biological sample to be tested for the presence of the analyte, said release medium comprising a labeled binding member disposed thereon for binding with the analyte;
   c. a capture medium received in said casing and in fluid communication with said release medium;
   d. a result site located on said capture medium;
   e. a second binding member disposed on one of said release medium and said capture medium and configured to directly or indirectly bind to one of said labeled binding member and the analyte;
   f. a scavenger binding member disposed on one of said release medium and said capture medium separate from said result site, said scavenger binding member configured to directly or indirectly bind to a predetermined threshold concentration of the analyte; and
   g. a capture binding member is immobilized at said result site,
   wherein capture and detection of the analyte at said result site occurs when the overall concentration of the analyte in the biological sample is greater than said predetermined threshold concentration.

18. The device of claim 17, wherein said second binding member is releasably placed on said release medium.

19. The device of claim 17, wherein said scavenger binding member is at least one of immobilized on said capture medium and releasably placed on said release medium.

20. The device of claim 17, wherein the presence of said labeled binding member at said result site is a positive indication that the concentration of the analyte in the biological sample is greater than said predetermined threshold concentration.

* * * * *